US005466588A

United States Patent [19]

Kosaki et al.

[11] Patent Number: 5,466,588
[45] Date of Patent: Nov. 14, 1995

[54] PRODUCTION OF HIGH OPTICAL PURITY D-LACTIC ACID

[75] Inventors: Michio Kosaki, Tokyo; Kimitoshi Kawai, Ibo, both of Japan

[73] Assignee: Daicel Chemical Industries, Ltd., Osaka, Japan

[21] Appl. No.: 250,094

[22] Filed: May 26, 1994

Related U.S. Application Data

[63] Continuation of Ser. No. 925,240, Aug. 4, 1992, abandoned, which is a continuation of Ser. No. 633,156, Dec. 21, 1990, abandoned, which is a continuation of Ser. No. 822,348, Jan. 24, 1986, abandoned.

[30] Foreign Application Priority Data

Feb. 8, 1985 [JP] Japan .................................. 60-22907
Jun. 21, 1985 [JP] Japan ................................. 60-135657
Jun. 21, 1985 [JP] Japan ................................. 60-135658

[51] Int. Cl.$^6$ ................................................. C12P 7/56
[52] U.S. Cl. .................. 435/139; 435/252.1; 435/170
[58] Field of Search ............................ 435/139, 853, 435/822, 170, 252.1

[56] References Cited

U.S. PATENT DOCUMENTS 3,262,862  7/1966  Kitahara et al. ..................... 435/139
4,467,034  8/1984  Voelskow et al. ................... 435/139
4,506,012  3/1985  Reed ..................................... 435/139

FOREIGN PATENT DOCUMENTS 1193992  9/1985  Canada ................................. 435/139

*Primary Examiner*—Irene Marx
*Attorney, Agent, or Firm*—Flynn, Thiel, Boutell & Tanis

[57] ABSTRACT

D-lactic acid is continuously produced by conducting fermentation in a D-lactic acid-producing medium by using as a seed culture a part of a broth obtained in a previous fermentation step of D-lactic acid and elevating a concentration of said growth-promoter to such an effect that a optical purity of the D-lactic acid may be prevented from decreasing. Instead, air may be used.

2 Claims, No Drawings

PRODUCTION OF HIGH OPTICAL PURITY D-LACTIC ACID

This application is a continuation of U.S. Ser. No. 07/925 240, filed Aug. 4, 1992, which is a continuation of U.S. Ser. No. 07/633 156, filed Dec. 21, 1990, which is a continuation of U.S. Ser. No. 06/822,348, filed Jan. 24, 1986 all now abandoned.

The invention relates to a process for producing D-lactic acid with a high optical purity by fermentation. In particular, the process is continuously carried out by the use of a fermentation broth of D-lactic acid as a seed culture in a subsequent fermentation. In addition, the invention provides an improvement also in the batchwise fermentation production of D-lactic acid.

STATEMENT OF PRIOR ARTS

It is known in Japanese patent publications A (unexamined) Nos. 58-16688 and 58-36394 that D-lactic acid is produced by lactic acid bacteria. U.S. Pat. No. 3,262.,862 teaches the use of lactic acid bacteria for fermentation of D-lactic acid.

It is noted that all conventional processes are conducted batchwise so that a prepropagation step accompanied by troublesome procedures such that a preserved lactic acid bacterium is allowed to grow while successively increasing the amount of the culturing broth should be carried out at each batch. In order to efficiently produce D-lactic acid, a continuous culturing of a fermentation medium has been attempted. However this process has not so far been applied at an industrial scale, since it is not possible to prevent the growth of infectious microbes for a prolonged period at present. Thus the production of D-lactic acid has been exclusively carried out batchwise.

Since no process for preventing infectious microbes for a prolonged period in continuous fermentation of D-lactic acid has been established as yet, semicontinuous fermentation was attempted by repeating batch fermentation. As a result, it was found that repetition of batch fermentation caused reduction in the optical purity of the product, i.e. D-lactic acid.

As a result of our studies to overcome these problems, we have found a process by which high-optical purity D-lactic acid can be produced by repeated batch fermentation, thus completing the present invention.

SUMMARY OF THE INVENTION

The invention provides a process for producing D-lactic acid, which comprises the step of conducting the fermention of D-lactic acid in a D-lactic acid-producing medium containing a carbohydrate, an inorganic salt, a growth-promoter and a neutralizing agent, by using as a seed culture a part of a broth obtained in a previous fermentation step of D-lactic acid in which a D-lactic acid-producing bacterium already grown in a pre-propagation step is used and elevating the concentration of said growth-promoter to such an amount that the optical purity of the D-lactic acid may be prevented from decreasing. It is preferred that the neutralizing agent is sodium hydroxide, sodium carbonate, sodium bicarbonate or ammonia. In a preferred embodiment of the invention, process air is introduced into the medium without the use of said broth and the elevation of the concentration of the growth-promoter.

According to the invention, D-lactic acid is produced by (1) first growing a D-lactic acid-producing bacterium by a pre-preparation step, (2) cultivating D-lactic acid with said bacterium in a culture medium which comprises a carbohydrate, an inorganic salt, a growth-promoter and a neutralizing agent and (3) conducting further fermentation of D-lactic acid in a culture medium which comprises a carbohydrate, an inorganic salt, a growth-promoter and a neutralizing agent, using as a seed culture a part of the broth obtained in the previous cultivation step and elevating the concentration of, said growth-promoter to such an amount that the optical purity of the D-lactic acid may be prevented from decreasing.

In other words, the invention provides a process for producing D-lactic acid wherein a D-lactic acid-producing bacterium previously grown by a prepropagation step is cultured in a medium comprising carbohydrates, inorganic salts, growth promoter(s) and neutralizing agent(s) and part of the broth thus obtained is employed as a seed culture in the subsequent D-lactic acid fermentation, wherein the concentration of the growth promoter(s) is elevated to an extent capable of inhibiting a decrease in the optical purity of D-lactic acid.

The invention provides an improvement in the process in which a part of the broth obtained in the previous fermentation of D-lactic acid is used as a seed culture. That is, the process is improved by introducing air into the cultivation medium or using a specified neutralizing agent selected from sodium hydroxide, sodium carbonate, sodium bicarbonate and ammonia. This improvement is effective in the batch method of the process as well. This improved batch method can be conducted effectively without the elevation of a concentration of the growth-promoter.

In the practical point of view, the batchwise process according to the invention is preferably carried out as illustrated below.

(1) D-lactic acid is produced by culturing a D-lactic acid-producing bacterium belonging to the genus Sporolactobacillus in a D-lactic acid-producing medium comprising a carbohydrate, an inorganic acid, a growth-promoter and a neutralizing agent and introducing air into the medium.

(2) D-lactic acid is produced by culturing a D-lactic acid-producing bacterium belonging to the genus Sporolactobacillus in a D-lactic acid-producing medium comprising a carbohydrate, an inorganic salt, a growth-promoter and a neutralizing agent selected from sodium hydroxide, sodium carbonate, sodium hydrogen-carbonate and ammonia.

The above shown process enables production of D-lactic acid with a high optical purity when it is repeated batchwise.

MICROORGANISM TO BE USED

Any D-lactic acid-producing bacterium may be used in the present invention. For example, *Sporolactobacillus inulinus* ATCC 15538, *Lactobacillus delbrüeckii L. leichmannii* JCM 1016, *L. leichmannii* JCM 1557 or *L. lactis* DSM-20073 may be used.

CULTURE METHOD

A seed culture of a D-lactic acid-producing bacterium is prepared in a conventional manner of batch fermentation. That is, the D-lactic acid-producing bacterium is cultured in, for example, a GYP medium as shown in Table 1. when the bacterium is sufficiently grown, the culturing broth is successively increased at a rate of 10 to 1000 times to thereby prepare the seed culture. Then the seed culture thus obtained is allowed to produce D-lactic acid in a D-lactic acid-producing medium. A composition of the medium should depend on a lactic-acid-producing bacterium used in the process. It is prepared from a carbohydrate, an inorganic salt, a growth promoter and a neutralizing agent. The carbohydrate preferably includes a sugar or saccharide such as glucose, fructose, sucrose, inulin, maltose, mannose, raffinose, trehalose and a substance containing therein any saccharide, for instance a starch hydrolyzate and molasses. The inorganic salt preferably includes magnesium sulfate, ammonium sulfate, potassium phosphate and ferrous sulfate. The growth promoter preferably includes yeast extract, peptone, meat extract and soybean powder. Each ingredient may be used with another in combination. The growth promoter is used since a lactic acid-producing bacterium generally exhibits high auxotrophy. It is further necessary to add neutralizing agent(s) thereto to thereby adjust the medium in a pH range of 4.5 to 7.0, since lactic acid-producing bacteria are acid sensitive. The neutralizing agent preferably includes $CaCO_3$, $Ca(OH)_2$, $NaOH$, $Na_2CO_3$, $NaHCO_3$, $KOH$ and ammonia.

The fermentation process of the invention is normally conducted under anaerobic condition, for instance by passing an inert gas such as nitrogen gas into the system. It is added, however, that air may be used in the above shown embodiment without any inert gas.

The fermentation temperature depends on the lactic acid-producing bacterium to be used. For example, it is preferable to carry out the fermentation at 37° C. when *Sporolactobacillus inulinus* ATCC 15538 is employed, while *L. delbrueckii* IFO 3534 is preferably cultured at 45° to 50° C. Upon completion of the first D-lactic acid fermentation in this manner, part of the obtained broth is used as a seed culture in the subsequent D-lactic acid fermentation. The D-lactic acid obtained from the second fermentation in a medium of the same composition as that used in the first fermentation shows a lowered optical purity. However, this problem can be solved by elevating the concentration of growth promoter(s). The concentration of growth promoters in a medium used in a process of repeated fermentation is higher by generally 20 % or more preferably 50% or more, than the initial concentration. Alternately other growth promoter(s) may be added thereto. The amount of the growth promoter(s) to be added depends on the bacterium to be used. Generally 0.1% or more, preferbly 0.5% or more, of the growth promoter(s) should be added.

TABLE 1

GYP medium

| | |
|---|---|
| glucose | 20 g/l |
| yeast extract | 10 g/l |
| peptone | 10 g/l |
| sodium acetate | 10 g/l |
| magnesium sulfate | 0.2 g/l |
| $FeSO_4 \cdot 7H_2O$ | 10 mg/l |
| $MnSO_4 \cdot 4.5H_2O$ | 10 mg/l |
| NaCl | 10 mg/l |

However it is also possible to prevent the D-lactic acid purity from falling by supplying air to the fermentation medium even in the case where $CaCO_3$ is used as a neutralizing agent without elevating the concentration of the growth promoter(s).

It is preferable to supply air to the medium at a rate of less than 10% by volume per min (hereinafter referred to as 0.1 V.V.M.) based on the amount of the liquid medium. It is undesirable that the rate exceeds 0.1 V.V.M., since the growth of the lactic acid-producing bacterium is completly inhibited thereby.

The term "air" as used herein refers to one containing 21% by volume of oxygen. As a matter of course, the maximum amount of the air supply is restricted depending on the concentration of oxygen in the air.

The use of this process makes it possible to produce high-optical purity D-lactic acid by the use of any neutralizing agent(s) without using a large amount of expensive growth promoter(s).

However it is also possible to prevent the optical purity of D-lactic acid from falling by employing neutralizing agent(s) selected from among sodium hydroxide, sodium carbonate, sodium hydrogencarbonate and ammonia even when the fermentation is repeated in a medium of the same composition as that used in the first fermentation.

This process makes it possible to effectively produce high-optical purity D-lactic acid without using a large amount of expensive growth promoter(s).

The neutralizing agent(s) as used herein may be in the form of an aqueous solution, a powder or a gas. It may be selected from the viewpoint of convenience in operation.

D-lactic acid is important as a starting material in synthesizing various optically active substances so that the demand therefor has been recently increasing. Under these circumstances, the present invention makes it possible to efficiently produce D-lactic acid on an industrial scale.

PREFERRED EMBODIMENTS OF THE INVENTION

To further illustrate the present invention, the following Examples will be given. In each Example, the optical purity of D-lactic acid was determined by subjecting the total lactic acid to HPLC with the use of an ion exchange resin (SAX 801) wherein the content of L-lactic acid was enzymatically determined with the use of an L-lactic acid dehydrogenase and the optical purity of D-lactic acid was determined according to the following equation:

$$\text{D-lactic acid optical purity (\%)} = \left( 1 - \frac{\text{L-lactic acid}}{\text{total lactic acid}} \right) \times 100$$

EXAMPLES 1 AND 2 AND COMPARATIVE EXAMPLE 1

*Sporolactobacillus inulinus* ATCC 15538 was inoculated into a GYP medium and static cultured therein at 37° C. for three days. 1 ml of the culturing broth was inoculated into 25 ml of a GYP medium containing 1% of $CaCO_3$ and static cultured therein at 37° C. for one day, thus preparing a seed culture. 150 ml of the obtained seed culture was inoculated into 3 1 of a fermentation medium having the following composition and fermentation was performed at 37° C. under agitating at 200 rpm.

| Fermentation medium | |
|---|---|
| glucose | 100 g/l |
| yeast extract | 5 g/l |

-continued

| Fermentation medium | |
|---|---|
| $MgSO_4 \cdot 7H_2O$ | 0.2 g/l |
| $FeSO_4 \cdot 7H_2O$ | 10 mg/l |
| $MnSO_4 \cdot 4.5H_2O$ | 10 mg/l |
| NaCl | 10 mg/l |
| $CaCO_3$ | 60 g/l |

37 hours after the initiation of the fermentation, the glucose was completely consumed and 98 g/l of lactic acid containing 99.2% of D-lactic acid was accumulated in the medium. After the completion of the first D-lactic acid fermentation, 150 ml portions of the resulting broth were added to 2850-ml portions of (A) the fermentation medium as shown above (Comparative Example 1), (B) the fermentation medium as shown above except that the concentration of the yeast extract was elevated to 7.5 g/l (Example 1), (C) the fermentation medium as shown above except that 5 g/l of peptone was further added thereto (Example 2) respectively, and allowed to ferment therein. The optical purities of D-lactic acid thus produced were (A) 97.3% (Comparative Example), (B) 99.7% (Example 1) and (C) 99.4% (Example 2).

EXAMPLES 3 AND 4 AND COMPARATIVE EXAMPLE 2

The first D-lactic acid fermentation was carried out in the same manner as described in Example 1. 39 hours after the initiation of the fermentation, the glucose was completely consumed and 97 g/l of lactic acid containing 99.3% of D-lactic acid accumulated in the medium. The D-lactic acid fermentation broth was subjected to the subsequent fermentation wherein yeast extract was employed in a concentration as shown in Table 2. Table 2 shows the result.

TABLE 2

| | Yeast extract concentration(%) | D-lactic acid optical purity in 2nd fermentation | D-lactic acid optical purity in 3rd fermentation |
|---|---|---|---|
| Comp. Ex. 2 | 0.5 | 97.8% | — |
| Ex. 3 | 0.6 | 99.0% | 99.2% |
| Ex. 4 | 0.75 | 99.3%* | 99.2% |

EXAMPLE 5

*Sporolactobacillus inulinus* ATCC 15538 was inoculated into a GYP medium and static cultured therein a 37° C. for three days. 2 ml of the culturing broth was inoculated into 50 ml of a GYP medium containing 1% of $CaCO_3$ and static cultured therein at 37° C. for one day, thus preparing a seed culture. 50 ml of the obtained seed culture was inoculated into 950 ml of a fermentation medium having the following composition and fermentation was performed at 37° C.

| Fermentation medium | |
|---|---|
| glucose | 100 g/l |
| yeast extract | 5 g/l |
| $MgSO_4 \cdot 7H_2O$ | 0.2 g/l |
| $FeSO_4 \cdot 7H_2O$ | 10 mg/l |
| $MnSO_4 \cdot 4.5H_2O$ | 10 mg/l |
| NaCl | 10 mg/l |
| $CaCO_3$ | 60 g/l |

39 hours after the initiation of the fermentation, the glucose was completely consumed and 95 g/l of lactic acid containing 99.1% of D-lactic acid was accumulated in the medium. After the completion of the first D-lactic acid fermentation, 50 ml of the resulting broth was added to 950 ml of the fermentation medium as defined above and the fermentation was repeated while supplying air at a rate of 0.03 V.V.M. (V.V.M. is volume per volume per minute). Thus D-lactic acid of a optical purity 99.0% was obtained.

EXAMPLE 6

The procedures of Example 5 were followed except that air was supplied at a rate of 0.075 V.V.M. Table 3 shows test results.

TABLE 3

| | 1st fermentation | 2nd fermentation | |
|---|---|---|---|
| | D-lactic acid optical purity (%) | air supply rate (V.V.M.) | D-lactic acid purity (%) |
| Ex. 5 | 99.1 | 0.030 | 99.0 |
| Ex. 6 | 98.9 | 0.075 | 99.0 |

EXAMPLE 7

*Sporolactobacillus inulinus* ATCC 15538 was inoculated into a GYP medium and static cultured therein at 37° C. for three days. 2 ml of the culturing broth was inoculated into 50 ml of a GYP medium containing 1% of $CaCO_3$ and static cultured therein at 37° C. for one day, thus preparing a seed culture. 50 ml of the obtained seed culture was inoculated into 950 ml of a fermentation medium having the following composition and fermentation was performed at 37° C. while controlling the pH value of the culture at 5.8 to 6.2 with an 8.5% aqueous solution of ammonia.

| Fermentation medium | |
|---|---|
| glucose | 100 g/l |
| yeast extract | 5 g/l |
| $MgSO_4 \cdot 7H_2O$ | 0.2 g/l |
| $FeSO_4 \cdot 7H_2O$ | 10 mg/l |
| $MnSO_4 \cdot 4.5H_2O$ | 10 mg/l |
| NaCl | 10 mg/l |

41 hours after the initiation of the fermentation, the glucose was completely consumed and 82 g/l of lactic acid containing 99.5% of D-lactic acid was accumulated in the medium. After the completion of the first D-lactic acid fermentation, 50 ml of the resulting broth was added to 950 ml of the fermentation medium as defined above and the fermentation was repeated. Thus D-lactic acid of a optical purity of 99.2% was obtained. The third fermentation was carried out in the same manner with the use of a broth obtained in the second fermentation as a seed culture. Thus, D-lactic acid of a optical purity of 99.3% was obtained.

EXAMPLE 8

A seed culture prepared in the same manner as described in Example 7 was cultured in a fermentation medium having the following composition while controlling the pH value of the culture at 5.8 to 6.6 with a 20% aqueous solution of sodium hydroxide at 37° C.

| | |
|---|---|
| glucose | 200 g/l |
| yeast extract | 10 g/l |
| MgSO$_4$·7H$_2$O | 0.2 g/l |
| FeSO$_4$·7H$_2$O | 10 mg/l |
| MnSO$_4$·4.5H$_2$O | 10 mg/l |
| NaCl | 10 mg/l |

50 hours after the initiation of the fermentation, the glucose was completely consumed and 128 g/l lactic acid containing 99.2% of D-lactic acid was accumulated in the medium. The fermentation was repeated five times in the same manner as described in Example 7. The purities of D-lactic acid obtained in the third and fifth fermentations were 98.9% and 99.1% respectively.

The embodiments of the invention in which an exclusive property or privilege is claimed are defined as follows:

1. A process for the production of D-lactic acid having a high optical purity comprising the steps of:

inoculating a glucose-yeast extract-peptone medium with *Sporolactobacillus inulinus* ATCC 15538 bacterium and culturing the bacterium therein to produce a culture broth;

inoculating a glucose-yeast extract-peptone medium containing 1% CaCO$_3$ with the culture broth and culturing the culture broth therein to produce a seed culture;

inoculating a glucose-yeast extract medium containing 100 g/l glucose, 5 g/l yeast extract, 0.2 g/l MgSO$_4$·7H$_2$O, 10 mg/l FeSO$_4$·7H$_2$O, 10 mg/l MnSO$_4$·4.5H$_2$O, 10 mg/l NaCl and 60 g/l CaCO$_3$ with the seed culture and conducting fermentation therein to produce a fermentation broth;

adding the fermentation broth to a glucose-yeast extract medium containing 100 g/l glucose, 7.5 g/l yeast extract, 0.2 g/l MgSO$_4$·7H$_2$O, 10 mg/l FeSO$_4$·7H$_2$O, 10 mg/l MnSO$_4$·4.5H$_2$O, 10 mg/l NaCl and 60 g/l CaCO$_3$ and conducting fermentation therein to produce D-lactic acid of a high optical purity; and recovering said D-lactic acid.

2. A process for the production of D-lactic acid having a high optical purity comprising the steps of:

inoculating a glucose-yeast extract-peptone medium with *Sporolactobacillus inulinus* ATCC 15538 bacterium and culturing the bacterium therein to produce a culture broth;

inoculating a glucose-yeast extract-peptone medium containing 1% CaCO$_3$ with the culture broth and culturing the culture broth therein to produce a seed culture;

inoculating a glucose-yeast extract medium containing 100 g/l glucose, 5 g/l yeast extract, 0.2 g/l MgSO$_4$·7H$_2$O, 10 mg/l FeSO$_4$, 10 mg/l 10 mg/l NaCl and 60 g/l CaCO$_3$ with the seed culture and conducting fermentation therein to produce a fermentation broth;

adding the fermentation broth to a glucose-yeast extract medium containing 100 g/l glucose, 5 g/l yeast extract, 0.2 g/l MgSO$_4$·7H$_2$O, 10 mg/l FeSO$_4$, 10 mg/l MnSO$_4$·4.5H$_2$O, 10 mg/l NaCl and 60 g/l CaCO$_3$ and conducting aerobic fermentation therein with air being supplied at a rate of from 0.03–0.075 V.V.M. to produce D-lactic acid of a high optical purity; and recovering said D-lactic acid.

\* \* \* \* \*

UNITED STATES PATENT AND TRADEMARK OFFICE
CERTIFICATE OF CORRECTION

PATENT NO. : 5,466,588
DATED : November 14, 1995
INVENTOR(S) : Michio KOSAKI, et al It is certified that error appears in the above-indentified patent and that said Letters Patent is hereby corrected as shown below:

Column 8, line 21; insert after the second occurrence of 10 mg/l ---$MnSO_4 \cdot 4.5H_2O,$---.

Signed and Sealed this

Twenty-first Day of May, 1996

Attest:

BRUCE LEHMAN

Attesting Officer      Commissioner of Patents and Trademarks